(12) United States Patent
Dodge et al.

(10) Patent No.: US 6,218,425 B1
(45) Date of Patent: Apr. 17, 2001

(54) 8-SUBSTITUTED B-NOR-6-THIAEQUILENIN COMPOUNDS HAVING ACTIVITY AS SELECTIVE ESTROGEN RECEPTOR MODULATORS

(75) Inventors: Jeffrey Alan Dodge, Indianapolis; Charles Willis Lugar, III, McCordsville, both of IN (US)

(73) Assignee: Eli Lilly and Company, Indianapolis, IN (US)

( * ) Notice: Subject to any disclaimer, the term of this patent is extended or adjusted under 35 U.S.C. 154(b) by 61 days.

(21) Appl. No.: 08/902,485

(22) Filed: Jul. 29, 1997

Related U.S. Application Data
(60) Provisional application No. 60/023,366, filed on Aug. 6, 1996.

(51) Int. Cl.[7] .................. A61K 31/38; C07D 333/50
(52) U.S. Cl. ........................................ 514/443; 549/42
(58) Field of Search ........................ 549/42; 514/443

(56) References Cited

U.S. PATENT DOCUMENTS

| | | | | |
|---|---|---|---|---|
| 1,444,277 | * | 2/1923 | Schmidt et al. | 549/42 |
| 2,480,746 | * | 8/1949 | Lee et al. | 549/42 |
| 5,679,694 | * | 10/1997 | Franzmann et al. | 514/339 |
| 5,834,488 | * | 11/1998 | Bell et al. | 514/324 |

OTHER PUBLICATIONS

R. C. Collins, et al., *J. Am. Chem. Soc.*, 79: 1103–1107 (1957).

M. K. Battacharjee, et al., *Tetrahedron*, 10: 215–222 (1960).

G. V. Bhide, et al., *Tetrahedron*, 10: 223–229 (1960).

G. V. Bhide, *Tetrahedron*, 10: 230–237 (1960).

R. R. Crenshaw, et al., *Tetrahedron Letters*, No. 52, 4495–4496 (1969).

* cited by examiner

*Primary Examiner*—Deborah C. Lambkin
(74) *Attorney, Agent, or Firm*—Gilbert T. Voy

(57) ABSTRACT

Certain B-nor-6-thiaequilenin compounds substituted at the 3-position with hydroxy and at the 8-position with hydroxy or alkoxy of from one to four carbon atoms are selective estrogen receptor modulators and are useful in the treatment of estrogen-related disorders including such conditions as osteoporosis, hyperlipidemia, estrogen-dependent breast cancer, uterine fibrosis, endometriosis, and restenosis.

12 Claims, No Drawings

8-SUBSTITUTED B-NOR-6-THIAEQUILENIN COMPOUNDS HAVING ACTIVITY AS SELECTIVE ESTROGEN RECEPTOR MODULATORS

Prov. Appln. No. 60/023,366 Aug. 6, 1996.

TECHNICAL FIELD

The present invention relates to organic compounds having biological activity, to formulations containing the compounds and to medical methods of treatment. More particularly, the present invention concerns a class of hydroxy- and alkoxy-substituted B-nor-6-thiaequilenin compounds, to pharmaceutical compositions containing the compounds, and to a method for their use as selective estrogen receptor modulators in the treatment of estrogen-related disorders.

BACKGROUND OF THE INVENTION

Equilenin, I, is an estrogenic steroidal hormone isolated from the urine of pregnant mares.

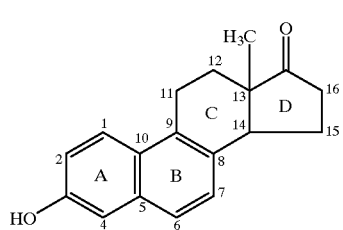

1

(Position numbering and ring letter designations in formula 1 above are in accordance with traditional nomenclature for steroids.)

Replacement of benzene rings by heterocyclic rings in synthetic estrogenic steroidal hormones have been reported by a number of workers, and Collins, et al., *J. Am. Chem. Soc.,* 79: 1103–1107 (1957) reported the synthesis of 3-desoxy-B-nor-6-equilenin, 2, in which the 3-hydroxy group is missing and a thiophene ring replaces the benzene "B ring" of equilenin:

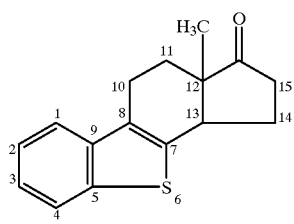

2

These compounds have been termed in the literature "B-nor-6-thiaequilenins" by virtue of the collapsing of ring B of equilenin by one carbon atom and the insertion of a sulfur atom.

Collins, et al. also reported the synthesis of the 13,14-dehydro compound, 3.

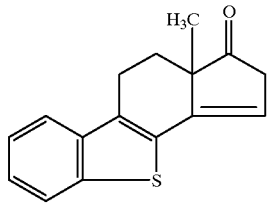

3

Crenshaw, et al., *Tetrahedron Letters,* 52:4495–4496 (1969) reported the corresponding alcohols derived from the reduction of the ketone functionality of B-nor-6-thiaequilenin, but reported that all of the compounds which they prepared were racemates at the ring fusion between the C and D rings.

BRIEF SUMMARY OF THE INVENTION

In its principle embodiment, the present invention provides class of the individual stereoisomers of 8-substituted B-nor-6-thiaequilenin compounds of the general formula

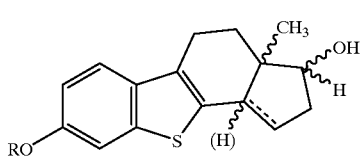

4 where R is hydrogen or straight or branched-chain alkyl of one to four carbon atoms.

The dotted line represents an optional double bond, and when the double bond is present, the parenthetical hydrogen atom is absent. The "squiggle" bonds represent that, in accordance with standard chemical notation, the atom or atoms so attached to the core molecular moiety lie in either possible stereochemical configuration.

The compounds are selective estrogen receptor modulators and, as such, are useful in the treatment of estrogen-related disorders including post-menopausal syndrome, osteoporosis, hyperlipidemia, estrogen-dependent breast cancer, uterine fibrosis, endometriosis, and restenosis.

In another embodiment, the present invention provides pharmaceutical compositions comprising an amount of a compound as defined above which is effective to treat conditions of estrogen-related disorders in combination with pharmaceutically acceptable carriers and excipients.

In yet another embodiment, the present invention provides a method of treating conditions of estrogen-related disorders which comprises administering to female in need of such treatment a therapeutically effective amount of a compound as defined above.

DETAILED DESCRIPTION

Throughout this specification and the appended claims, the naming convention for compounds of this invention employed is based on the numbering scheme:

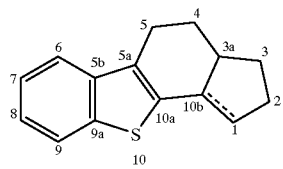

and the designations beta ("β") and alpha ("α") represent absolute configurations of the designated substituent either above or below the main plane of the fused ring system, respectively.

In the compounds of the present invention, when the optional double bond is present, the compounds possess the structural formula:

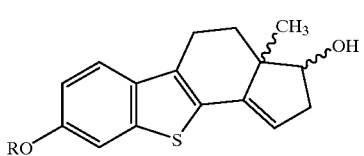

4a

In this embodiment, the compounds possess chiral centers at positions 3 (hydroxyl substituent) and 3a (methyl substituent) and thus four stereoisomers are possible: 1) 3α, 3aα; 2) 3α, 3aβ; 3) 3β, 3aα; and 4) 3β, 3aβ.

When the double bond is absent, the compounds possess the structural formula.:

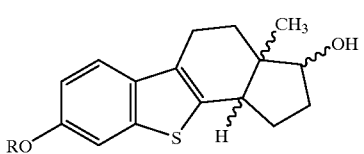

4b

In this embodiment, the compounds possess chiral centers at positions 3 (hydroxyl substituent), 3a (methyl substituent) and 10a and thus eight stereoisomers are possible: 1) 3α, 3aα, 10aα; 2) 3α, 3aα, 10aβ; 3) 3α, 3aβ, 10aα; 4) 3α, 3aβ, 10aβ; 5) 3β, 3aα 10aα; 6) 3β, 3aα 10aβ; 7) 3β, 3aβ, 10aα and 8) 3β, 3aβ, 10aβ.

While the substituent designated "R" may be hydrogen or alkyl of one to four carbon atoms, the preferred values for R are hydrogen and methyl.

Compounds contemplated as falling within the scope of the present invention include, but are not limited to the following examples:

3α-hydroxy-8-methoxy-3aα-methyl-2,3,3a,4,5,10bα-hexahydro-1H-benz[b]indeno[5,4-d]thiophene;

3α-hydroxy-8-methoxy-3aα-methyl-2,3,3a,4,5,10bβ-hexahydro-1H-benz[b]indeno[5,4-d]thiophene;

3α-hydroxy-8-methoxy-3aβ-methyl-2,3,3a,4,5,10bα-hexahydro-1H-benz[b]indeno[5,4-d]thiophene;

3α-hydroxy-8-methoxy-3aβ-methyl-2,3,3a,4,5,10bβ-hexahydro-1H-benz[b]indeno[5,4-d]thiophene;

3β-hydroxy-8-methoxy-3aα-methyl-2,3,3a,4,5,10bα-hexahydro-1H-benz[b]indeno[5,4-d]thiophene;

3β-hydroxy-8-methoxy-3aα-methyl-2,3,3a,4,5,10bβ-hexahydro-1H-benz[b]indeno[5,4-d]thiophene;

3β-hydroxy-8-methoxy-3aβ-methyl-2,3,3a,4,5,10bα-hexahydro-1H-benz[b]indeno[5,4-d]thiophene;

3β-hydroxy-8-methoxy-3aβ-methyl-2,3,3a,4,5,10bβ-hexahydro-1H-[-benz[b]indeno[5,4-d]thiophene;

3α,8-dihydroxy-3aα-methyl-2,3,3a,4,5,10bα-hexahydro-1H-benz[b]indeno[5,4-d]thiophene;

3α,8-dihydroxy-3aβ-methyl-2,3,3a,4,5,10bβ-hexahydro-1H-benz[b]indeno[5,4-d]thiophene;

3α,8-dihydroxy-3aβ-methyl-2,3,3a,4,5,10bα-hexahydro-1H-benz[b]indeno[5,4-d]thiophene;

3α,8-Dihydroxy-3aβ-methyl-2,3,4a,4,5,10bβ-hexahydro-1H-benz[b]indeno[5,4-d]thiophene;

3β,8-dihydroxy-3aα-methyl-2,3,3a,4,5,10bα-hexahydro-1H-benz[b]indeno[5,4-d]thiophene;

3β,8-dihydroxy-3aα-methyl-2,3,3a,4,5,10bβ-hexahydro-1H-benz[b]indeno[5,4-d]thiophene;

3β,8-Dihydroxy-3aβ-methyl-2,3,3a,4,5,10bα-hexahydro-1H-benz[b]indeno[5,4-d]thiophene;

3β,8-dihydroxy-3aβ-methyl-2,3,3a,4,5,10bβ-hexahydro-1H-benz[b]indeno[5,4-d]thiophene;

3α-Hydroxy-8-methoxy-3aα-methyl-3,3a,4,5-tetrahydro-2H-benz[b]indeno[5,4-d]thiophene;

3α-Hydroxy-8-methoxy-3aβ-methyl-3,3a,4,5-tetrahydro-2H-benz[b]indeno[5,4-d]thiophene;

3β-Hydroxy-8-methoxy-3aα-methyl-3,3a,4,5-tetrahydro-2H-benz[b]indeno[5,4-d]thiophene;

3β-Hydroxy-8-methoxy-3aβ-methyl-3,3a,4,5-tetrahydro-2H-benz[b]indeno[5,4-d]thiophene;

3α,8-Dihydroxy-3aα-methyl-3,3a,4,5-tetrahydro-2H-benz[b]indeno[5,4-d]thiophene;

3α,8-Diydroxy-3aβ-methyl-3,3a,4,5-tetrahydro-2H-benz[b]indeno[5,4-d]thiophene;

3β,8-Dihydroxy-3aα-methyl-3,3a,4,5-tetrahydro-2H-benz[b]indeno[5,4-d]thiophene; and 3β,8-Dihydroxy-3aα-methyl-3,3a,4,5-tetrahydro-2H-benz[b]indeno[5,4-d]thiophene.

Synthesis of Compounds of the Invention

The general Reaction Schemes set out below describe the synthesis of the various individual stereoisomers of compounds contemplated as falling within the scope of the present invention. Specific examples for the preparation of compounds of the invention are detailed in Examples 1–11 below.

The synthesis of compounds in accordance with the present invention can be thought of as being divisible into two series based upon the stereochemistry of the 3a-methyl in structural formulae 4a and 4b above.

Compounds of the present invention where the configuration of the 3a-methyl group is beta are synthesized by the general reaction sequence depicted below in Reaction Scheme 1. The starting material, (S)-2,3,7,7a-tetrahydro-7a-methyl-1H-indene, 5(S), is prepared using the method described in *Organic Syntheses*, 7: 363 (1984). The stereochemistry of the 3a-methyl group is carried through the series of compounds depicted in Reaction Scheme 1.

Compound 5 is epoxidized by the action of hydrogen peroxide in base to the corresponding epoxide, 6(S). Compound 6(S) is reacted with the desired 3-alkoxybenzenethiol, 7, in the presence of base to produce the corresponding indanone, 8(S).

Compound 8(S) is cyclized by the action of aluminum chloride to the tetracyclic compound, 9(S), and reduction of 9(S) with sodium borohydride produces the hydroxy compound, 10(S). In this reduction, the stereochemistry of the 3a-methyl group controls the stereochemistry of the reduction such that the predominant product is the one in which the 3a-methyl group and the new hydroxyl substituent at position 3 have the same (i.e. "beta") configuration.

Reduction of the double bond in the carbocyclic five-membered ring of compound 10(S) by the action of hydrogen on a transition metal catalyst results in a mixture of the cis-compound 11a(S) and the trans- compound 11b(S) which are separated by typical chromatographic techniques.

The 8-hydroxy compounds 12a(S) and 12b(S) are produced by reacting the corresponding 8-alkoxy compounds 11a(S) and 11b(S) with sodium ethanethiolate.

The 8-alkoxy compounds in which the 3a-hydroxyl group is in the opposite, or "alpha," configuration, compounds 13a(S) and 13b(S) are prepared by inversion of the 3-position carbon atom by reaction of the 3-hydroxy group with 4-nitrobenzoic acid under Mitsunobu conditions (O. Mitsunobu, et al., *Bull. Chem. Soc., Japan,* 40: 935 (1967); O. Mitsunobu, et al., ibid., 2380).

The corresponding 8-hydroxy compounds, 14a(S) and 14b(S) are prepared from the corresponding 8-alkoxy compounds 13a(S) and 13b(S) in a manner analogous to the conversion of 11a(S) and 11b(S) to 12a(S) and 12b(S) described above.

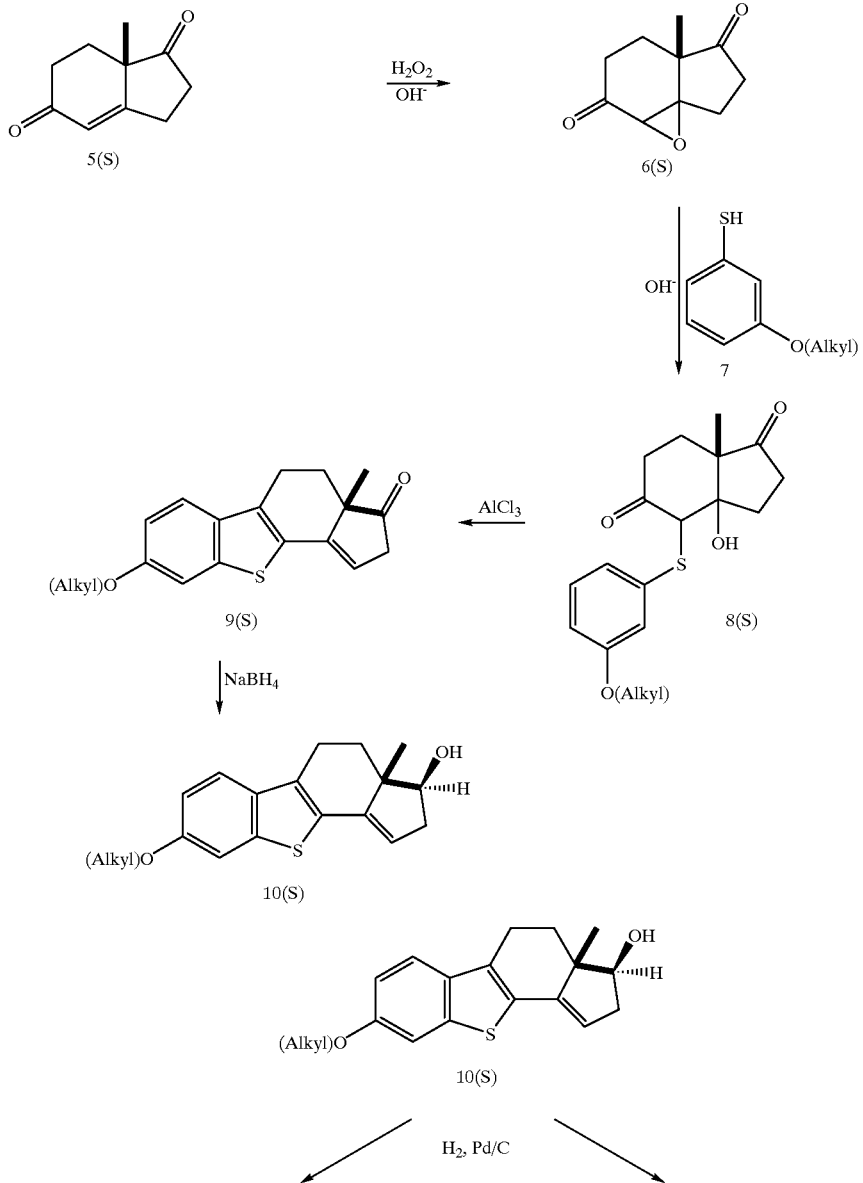

Reaction Scheme 1

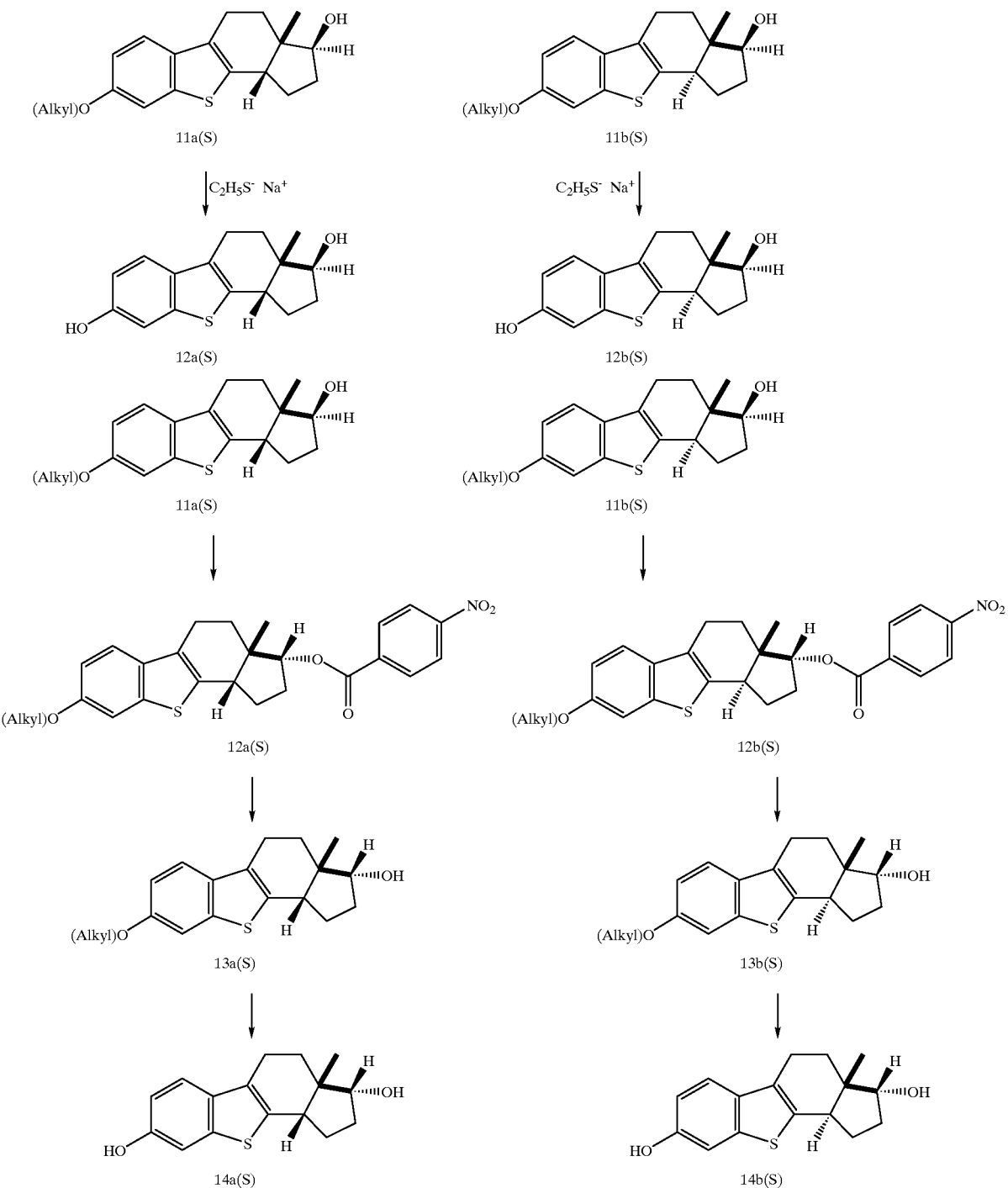
Compounds of the present invention where the configuration of the 3a-methyl group is alpha are synthesized by the general reaction sequence depicted below in Reaction Scheme 2 and parallels the sequence shown above for Reaction Scheme 1 with the exception that the starting material is the (R)-enantiomer of 2,3,7,7a-tetrahydro-7a-methyl-1H-indene.

Reaction Scheme 2
Synthesis of the "R-Series"
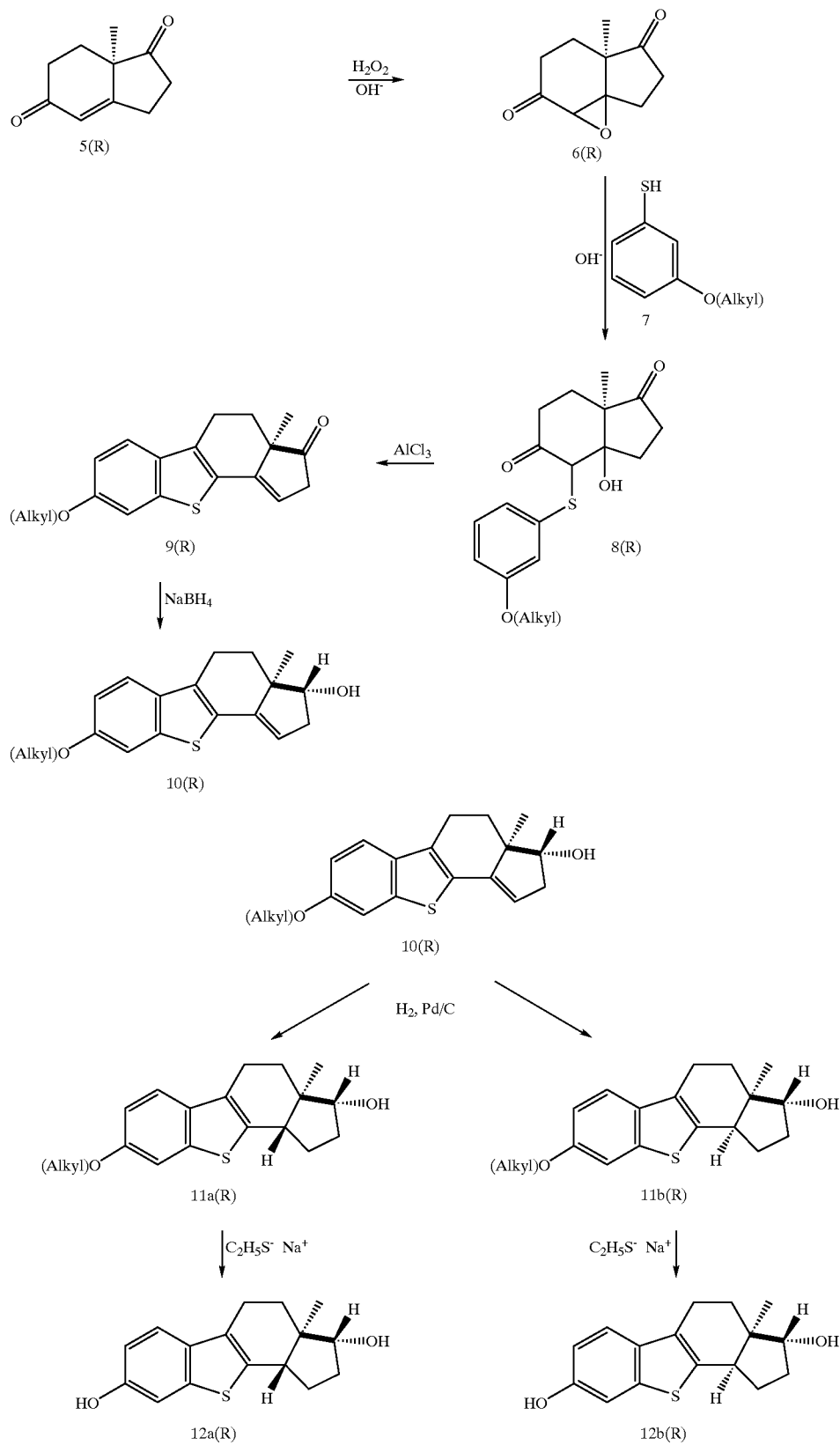

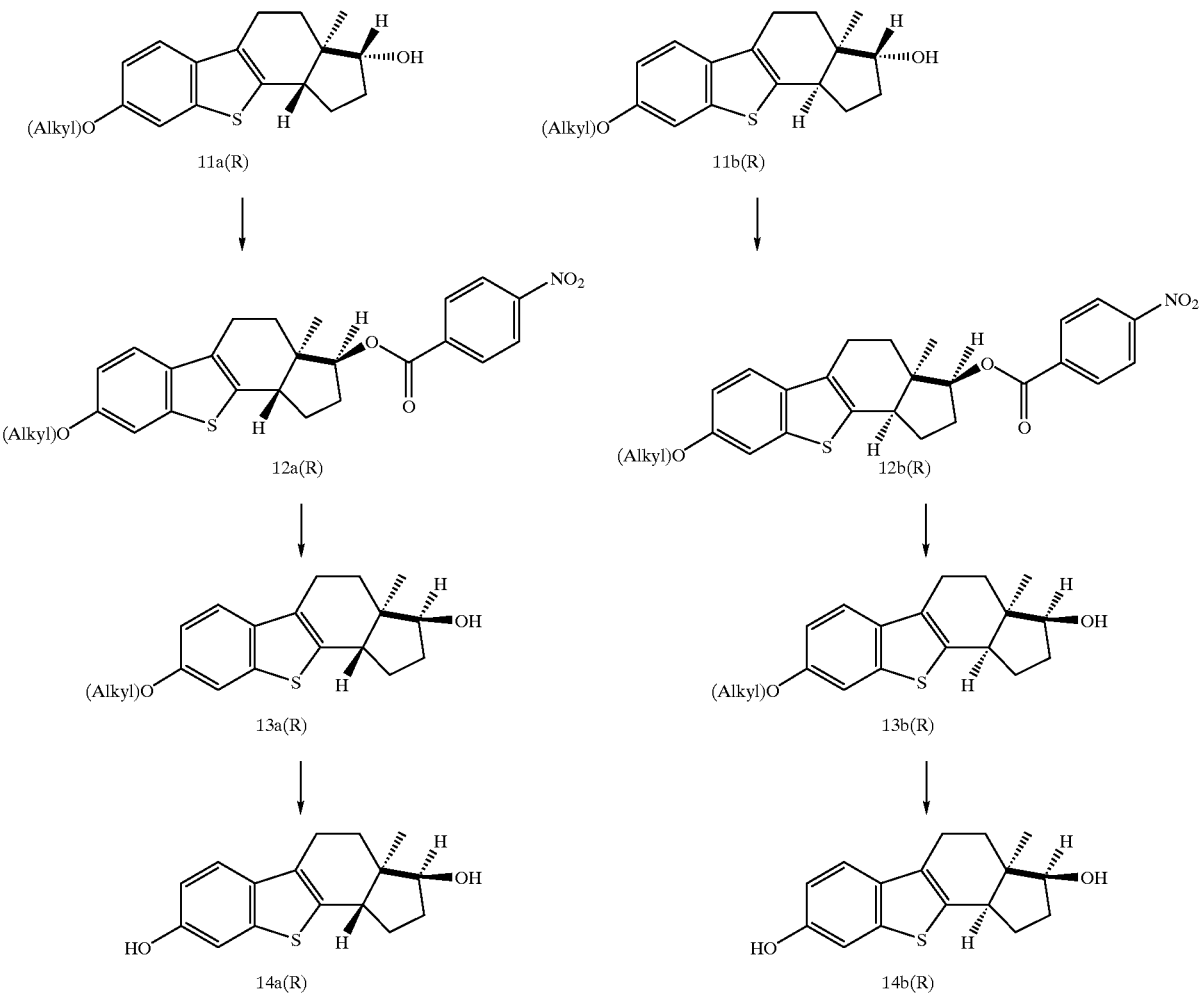

Pharmaceutical Formulations

The present invention also provides pharmaceutical compositions which comprise compounds of the present invention formulated together with one or more non-toxic pharmaceutically acceptable carriers and/or excipients. The formulations may be specially formulated for oral administration, in solid or liquid form, for parenteral injection, or for rectal or vaginal administration by means of a suppository.

The pharmaceutical compositions of this invention can be administered to humans and other mammals orally, rectally, intravaginally, parenterally, topically (by means of powders, ointments, creams, or drops), bucally or sublingually, or as an oral or nasal spray. The term "parenteral administration" refers herein to modes of administration which include intravenous, intramuscular, intraperitoneal, instrasternal, subcutaneous, or intraarticular injection or infusion.

Pharmaceutical compositions of this invention for parenteral administration comprise sterile aqueous or non-aqueous solutions, dispersions, suspensions, or emulsions, as well as sterile powders which are reconstituted immediately prior to use into sterile solutions or suspensions. Examples of suitable sterile aqueous and non-aqueous carriers, diluents, solvents or vehicles include water, physiological saline solution, ethanol, polyols (such as glycerol, propylene glycol, poly(ethylene glycol), and the like), and suitable mixtures thereof, vegetable oils (such as olive oil), and injectable organic esters such as ethyl oleate. Proper fluidity is maintained, for example, by the use of coating materials such as lecithin, by the maintenance of proper particle size in the case of dispersions and suspensions, and by the use of surfactants.

Parenteral compositions may also contain adjuvants such as preservatives, wetting agents, emulsifying agents, and dispersing agents. Prevention of the action of microorganisms is ensured by the inclusion of antibacterial and antifungal agents, for example, paraben, chlorobutanol, phenol sorbic acid, and the like. It may also be desirable to include isotonic agents such as sugars, sodium chloride, and the like. Prolonged absorption of injectable formulations may be brought about by the inclusion of agents which delay absorption such as aluminum monostearate and gelatin.

In some cases, in order to prolong the effect of the drug, it is desirable to slow the absorption of the drug following subcutaneous or intramuscular injection. This may be accomplished by the use of a liquid suspension or crystalline or amorphous material of low water solubility or by dissolving or suspending the drug in an oil vehicle. In the case of the subcutaneous or intramuscular injection of a suspension containing a form of the drug with low water solubility, the rate of absorption of the drug depends upon its rate of dissolution.

Injectable "depot" formulations of the compounds of this invention are made by forming microencapsulated matrices of the drug in biodegradable polymers such as poly(lactic acid), poly(glycolic acid), copolymers of lactic and glycolic acid, poly (orthoesters), and poly (anhydrides) these materials which are described in the art. Depending upon the ratio of drug to polymer and the characteristics of the particular polymer employed, the rate of drug release can be controlled.

Injectable formulations are sterilized, for example, by filtration through bacterial-retaining filters, or by presterilization of the components of the mixture prior to their admixture, either at the time of manufacture or just prior to administration (as in the example of a dual chamber syringe package).

Solid dosage forms for oral administration include capsules, tablets, pills, powders, and granules. In such solid dosage forms, the active component is mixed with at least one inert, pharmaceutically acceptable carrier such as sodium citrate, or dicalcium phosphate, and/or (a) fillers or extenders such as starches, lactose, glucose, mannitol, and silicic acid, (b) binding agents such as carboxymethylcellulose, alginates, gelatin, poly(vinylpyrrolidine), sucrose and acacia, (c) humectants such as glycerol, (d) disintegrating agents such as agar-agar, calcium carbonate, potato or tapioca starch, alginic acid, silicates and sodium carbonate, (e) solution retarding agents such as paraffin, (f) absorption accelerating agents such as quaternary ammonium compounds, (g) wetting agents such as cetyl alcohol and glycerin monostearate, (h) absorbents such as kaolin and bentonite clay, and (i) lubricants such as talc, calcium stearate, magnesium stearate, solid poly(ethylene glycols), sodium lauryl sulfate, and mixtures thereof. In the case of capsules, tablets and pills, the dosage form may also contain buffering agents.

Solid compositions of a similar type may also comprise the fill in soft or hard gelatin capsules using excipients such as lactose as well as high molecular weight poly(ethylene glycols) and the like.

Solid dosage forms such as tablets, dragees, capsules, pills and granules can also be prepared with coatings or shells such as enteric coatings or other coatings well known in the pharmaceutical formulating art. The coatings may contain opacifying agents or agents which release the active ingredient(s) in a particular part of the digestive tract, as for example, acid soluble coatings for release of the active ingredient(s) in the stomach, or base soluble coatings for release of the active ingredient(s) in the intestinal tract.

The active ingredient(s) may also be microencapsulated in a sustained-release coating, with the microcapsules being made part of a pill of capsule formulation.

Liquid dosage forms for oral administration of the compounds of this invention include solution, emulsions, suspensions, syrups and elixirs. In addition to the active components, liquid formulations may include inert diluents commonly used in the art such as water or other pharmaceutically acceptable solvents, solubilizing agents and emulsifiers such as ethanol, isopropanol, ethyl carbonate, ethyl acetate, benzyl alcohol, benzyl benzoate, propylene glycol, 1,3-butylene glycol, dimethyl formamide, oils (in particular, cottonseed, ground nut, corn, germ, olive, castor, and sesame oils), glycerol, tetrahydrofurfuryl alcohol, poly(ethylene glycols), fatty acid esters of sorbitol, and mixtures thereof.

Besides inert diluents, the liquid oral formulations may also include adjuvants such as wetting agents, emulsifying and suspending agents, and sweetening, flavoring, and perfuming agents.

Liquid suspension, in addition to the active ingredient(s) may contain suspending agents such as ethoxylated isostearyl alcohols, polyoxyethylene sorbitol and sorbitan esters, microcrystalline cellulose, aluminum metahydroxide, bentonite clay, agar-agar, and tragacanth, and mixtures thereof.

Compositions for rectal or intravaginal administration are prepared by mixing one or more compounds of the present invention with suitable non-irritating excipients such as cocoa butter, polyethylene glycol or any suppository wax which is a solid at room temperature, but liquid at body temperature and therefore melt in the rectum or vaginal cavity to release the active component(s). The compounds are dissolved in the melted wax, formed into the desired shape, and allowed to harden into the finished suppository formulation.

Compounds of the present invention may also be administered in the form of liposomes. As is know in the art, liposomes are generally derived from phospholipids or other lipid substances. Liposome formulations are formed by mono- or multilamellar hydrated liquid crystals which are dispersed in an aqueous medium. Any non-toxic, pharmaceutically acceptable, and metabolizable lipid capable of forming liposomes can be used. The present compositions in liposome form can contain, in addition to one or more active compounds of the present invention, stabilizers, excipients, preservatives, and the like. The preferred lipids are phospholipids and the phosphatidyl cholines (lecithins), both natural and synthetic.

Methods for forming liposomes are know in the art as described, for example, in Prescott, Ed., *Methods in Cell Biology*, Volume XIV, Academic Press, New York, N.Y. (1976), p. 33 et seq.

Dosage forms for topical administration of the compounds of the present invention include powders, sprays, ointments, creams, and inhalants. The active ingredient(s) is mixed under sterile conditions with a suitable pharmaceutically acceptable carrier and preservatives, buffers, or propellants as needed. Opthalmic formulations, eye ointments, and solutions are also contemplated as falling within the scope of the present invention.

Actual dosage levels of compounds of the present invention are varied so as to administer an amount of the compound which is effective to bring about the desired therapeutic affect. The dose required for a given patient will vary depending upon the severity of the condition being treated, the age, weight, and sex of the patient, as well as the state of health of the patient. However, it is within the skill of the art to "dose titrate" the patient; that is, to begin administering a dose known to be below the amount required to bring about the desired therapeutic effect and to gradually increase the dose until the desired effect is achieved.

Generally, for the treatment of estrogen-related disorders, compounds of the present invention are administered at dosage levels between about 10 mg/kg of body weight and about 250 mg/kg of body weight per day. If desired, the daily dosage may be divided into multiple doses for purposes of administration, e.g. into two to four doses per day.

Estrogen Receptor Binding

Representative compounds of the present invention were tested in an estrogen receptor binding assay in which the test compounds were allowed to compete for binding with tritiated 17β-estradiol.

In the assay, serial dilutions of the test compound were mixed with 0.5 nM of $^3$H-17β-estradiol, along with 0.5 mg/mL of protein from MCF-7 lysates, to a total volume of 0.14 mL. Binding was allowed to take place for 18 hours at 5° C., followed by the addition of 0.07 mL of dextran/charcoal and centrifugation to remove non-bound radioligand. Aliquots of supernate containing bound radioligand were mixed with scintillant and counted. Relative binding affinity (RBA) was calculated as:

$$RBA = \frac{IC_{50} 17 \text{ b} - \text{estradiol}}{IC_{50} \text{test compound}}.$$

The data for representative compounds of the present invention are presented in Table 1.

TABLE 1

| Estrogen Binding | |
|---|---|
| Compound | RBA |
| Example 7 | 11 |
| Example 8 | 16 |
| Example 9 | 9 |
| Example 10 | 4 |
| Example 11 | 4 |

Based upon the estrogen binding activity of the compounds of the present invention, the following illustrate methods of use for the compounds of formula I in experimental models or in clinical studies. These examples are for the purposes of illustration and are not meant to be limiting in any way.

Postmenopausal Syndrome
(Representative pathologies associated with estrogen deprivation)

A. Osteoporosis

Experimental models of postmenopausal osteoporosis are known in the art. Germane to this invention is the ovariectomized rat model which is provided in U.S. Pat. No. 5,393,763. The compounds of formula I are active in this model and demonstrate an effective treatment or prevention of bone loss due to the deprivation of estrogen.

An additional demonstration of the method of treating or preventing osteoporosis due to estrogen deprivation is carried out as follows: One hundred patients are chosen, representing healthy postmenopausal women, aged 45–60 and who are normally considered candidates for estrogen replacement therapy. This includes women with an intact uterus, who have had EL last menstrual period more than six months, but less than six years. Patients excluded for the study are those who have taken estrogens, progestins, or corticosteroids six months prior to the study or who have ever taken bis-phosphonates.

Fifty women (test group) of the test group receive 80–500 mg of a compound of formula I, for example, Formulation 1 (above), per day. The other fifty women (control group) receive a matched placebo per day. Both groups receive calcium carbonate tablets (648 mg) per day. The study is a double-blind design. Neither the investigators nor the patients would know to which group each patient is assigned.

A baseline examination of each patient includes quantitative measurement of urinary calcium, creatinine, hydroxyproline, and pyridinoline cross links. Blood samples are measured for serum levels of osteocalcin and bone-specific alkaline phosphatase. Baseline measurements also include a uterine examination and bone mineral density determination by photon absorptiometry. The study is continued for six months, and each of the patients is examined for changes in the above parameters.

During the course of treatment, activity of the test compounds is evinced by a decreased change in the biochemical markers of bone resorption in patients in the treatment group as compared to the control group and little or no decrease in bone mineral density compared to the control group.

B. Hyperlipidemia

Experimental models of postmenopausal hyperlipidemia are known in the art. Germane to this invention is the ovariectomized rat model which is detailed in U.S. Pat. No. 5,464,845.

Data presented in Table 2 below show comparative results among ovariectomized rats, rats treated with 17-a-ethynyl estradiol ($EE_2$), and rats treated with certain compounds of this invention. Although $EE_2$ caused a decrease in serum cholesterol when orally administered at 0.1 mg/kg/day, it also exerted a stimulatory effect on the uterus so that $EE_2$ uterine weight was substantially greater than the uterine weight of the ovariectomized animals. This uterine response to estrogen is well recognized in the art.

Not only did the compounds of the present invention reduce serum cholesterol compared to the ovariectomized animals, but the uterine weight was increased to lesser extent than those given $EE_2$. Compared to estrogenic compounds known in the art, the benefit of serum cholesterol reduction while lessening the effect on uterine weight is unusual and desirable.

As expressed in the data below, estrogenicity also was assessed by evaluating the response of eosinophil infiltration into the uterus. The compounds of this invention did not cause as large an increase in the number of eosinophils observed in the stromal layer of the ovariectomized, rat uteri. $EE_2$ caused a substantial and expected increase in eosinophil infiltration.

The data presented in Table 2 reflect the response per treatment group.

TABLE 2

| Compound | Dose (mg/kg[a]) | Uterine Weight Increase[b] | Uterine Eosinophil ($V_{max}$)[c] | Serum Cholesterol % Decrease[d] |
|---|---|---|---|---|
| $EE_2$[a] | 0.1 | 125.8* | 111.2* | 88.1* |
| Example 1 | 0.01 | −4.6 | 4.5 | 30.0 |
|  | 0.1 | 6.3 | 5.4 | 5 |
|  | 1.0 | 34.9* | 4.8 | 27.5 |
|  | 10.0 | 52.7 | 25.2 | 60.3* |
| Example 4a | 0.1 | 10.4 | 3.6 | −5.5 |
|  | 1.0 | 14.8 | 3.3 | −8.1 |
|  | 10.0 | 37.6 | 2.4 | 63.8* |
| Example 4b | 0.1 | −2.6 | 3.9 | −12 |
|  | 1.0 | 10.7 | 3.9 | −4.3 |
|  | 10.0 | 116.3* | 30.0 | 73.1* |
| Example 5 | 0.01 | −5.9 | 2.1 | 14.8 |
|  | 0.1 | 1.7 | 3.6 | −18.5 |
|  | 1.0 | 13.7 | 4.5 | 40.9* |
|  | 10.0 | 103.6* | 18.3 | 87.0* |
| Example 6 | 0.1 | 4.8 | 3.0 | −0.3 |
|  | 1.0 | 9.8 | 1.2 | −4.7 |
|  | 10.0 | 86.9* | 8.1 | 63.7* |
| Example 7 | 0.01 | −3.2 | 4.8 | 24.3* |
|  | 0.1 | 4.4 | 4.8 | 13 |
|  | 1.0 | 9.1 | 3.6 | 45.9* |
|  | 10.0 | 123.0 | 123.0* | 80.7* |
| Example 8 | 0.01 | 13.7 | 4.2 | −1 |
|  | 0.1 | 1.4 | 4.5 | 10.6 |
|  | 1.0 | 0.2 | 3.0 | 16.9 |
|  | 10.0 | 48.4* | 14.7 | 30.7* |
| Example 9 | 0.01 | 5.5 | 4.5 | 5.7 |
|  | 0.1 | 10.2 | 3.3 | 12.4 |

TABLE 2-continued

| Compound | Dose (mg/kg[a]) | Uterine Weight Increase[b] | Uterine Eosinophil $(V_{max})$[c] | Serum Cholesterol % Decrease[d] |
|---|---|---|---|---|
| | 1.0 | −5.3 | 3.9 | 32.1 |
| | 10.0 | 103.1* | 106.5* | 90.9* |

[a]17-a-Ethynyl estradiol
[b]Uterine Weight % increase versus the ovariectomized controls
[c]Eosinophil peroxidase, $V_{maximum}$
[d]Serum cholesterol decrease versus ovariectomized controls
*p < .05

An additional demonstration of the method of treating hyperlipidemia due to estrogen deprivation is as follows: One hundred patients are chosen, who are represent healthy postmenopausal women, aged 45–60, and who normally are considered candidates for estrogen replacement therapy. This group includes women with an intact uterus, who have not had a menstrual period for more than six months, but less than six years. Patients excluded for the study are those who have taken estrogens, progestins, or corticosteroids.

In the study, fifty women (test group) receive 80–500 mg of a compound of the present invention per day. The other fifty women (control group) receive a matched placebo per day. The study is a double-blind design. Neither the investigators nor the patients know to which group each patient is assigned.

A baseline examination of each patient includes serum determination of cholesterol and tri-glyceride levels. At the end of the study period (six months), a serum level profile is taken of each patient. Activity of the test compounds is evinced by data showing a lowering of the serum lipids, for example, cholesterol and/or tri-glycerides, in the test group versus the control.

Provided below are further examples of estrogen-dependent pathologies demonstrating additional utilities of the instant compounds.

Estrogen-dependent Breast Cancer

A. MCF-7 Proliferation Assay Test Procedure MCF-7 breast adenocarcinoma cells (ATCC HTB 22) are maintained in MEM (minimal essential medium, phenol-red free, Sigma St. Louis Mo.) supplemented with 10% fetal bovine serum (FBS) (v/v), L-glutamine (2 mM), sodium pyruvate (1 nM), HEPES (10 mM), non-essential amino acids, and bovine insulin (1 ug/mL). Ten days prior to the assay, the MCF-7 cells are switched to maintenance medium supplemented with 10% dextran-coated charcoal stripped fetal bovine serum (DCC-FBS) assay medium in place of the 10% FBS to deplete internal stores of estrogen. MCF-7 cells are removed from the maintenance flasks using a cell dissociating medium (Ca/Mg free HBSS; phenol-red free) supplemented with 10 mM HEPES and 2 mM EDTA. Cells are washed twice with the assay medium and adjusted to 80,000 cells/mL. Approximately 100 uL (8,000 cells)are added to a flat-bottomed micro culture well (Costar 3596) and incubated at 37° C. in a 5% $CO_2$ humidified incubator for 48 hours to allow cell adherence and equilibrium after transfer. Serial dilutions of the compounds of formula I: or DMSO as a diluent control are prepared in assay medium and 50 uL transferred to triplicate micro cultures followed by 50 uL of assay medium for a final volume of 200 uL. After an additional 48 hours of incubation, the micro cultures are pulsed with tritiated thymidine (1 uCi/well) for 4 hours. Cultures are terminated by freezing at −70° C. for 24 hours followed by thawing and harvesting of micro cultures using a Skatron Semiautomatic Cell Harvester. Samples are counted by liquid scintillation. Fifty percent inhibitory concentration of the test drugs ($IC_{50}$) are determined versus the control (DMSO).

In this assay, the compound of Example 7 wash shown to inhibit breast cancer cell proliferation at a dose level of 500 nM.

B. DMBA-Induced Mammary Tumor Inhibition Test Procedure

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between the groups.

Compounds of formula I are administered either through intraperitoneal injections in 2% acacia, or orally. Orally administered compounds are either dissolved or suspended in 0.2 mL of corn oil. Each treatment, including acacia and corn oil control treatments, is administered once daily to each animal. Following the initial tumor measurement and selection of test animals, tumors are measured each week by the above mentioned method. The treatment and measurements of animals is continued for 3 to 5 weeks at each time the areas of the tumors are determined. For each compound and control, the change in the mean tumor area is determined.

Uterine Fibrosis

A. First Test Procedure

Women between the ages of 25–40 years of age and who are in general good health but who have been diagnosed as suffering from uterine fibroid disease, are chosen for this study. Methods for diagnosis of uterine fibroid disease include usual techniques, which include CT and MRI imaging, hysteroscopy, hysterosalpingography, ultrasound, or laparoscopy. Women selected for the study are evaluated by the attending physician as good candidates for surgical intervention to remove the myomas. Excluded from this study are those women, who are taking any form of hormonal therapy for treatment of uterine fibroids or for any other reason.

Half of the women taking part in the study receive 80–500 mg of a compound of formula I per day and fifty women would receive a matched placebo. The study is continued for three months. At the end of the study period, each patient is evaluated by parameters listed above and the status of the fibrosis determined.

B. Second Test Procedure

1. Induction of Fibroid Tumors in Guinea Pigs

Prolonged estrogen stimulation is used to induce leiomyomata in sexually mature female guinea pigs. Animals are dosed with estradiol 3–5 times per week by injection, for 2–4 months or until tumors arise. Treatments consisting of a compound of formula I or vehicle are administered daily for 3–16 weeks. Animals are sacrificed at the end of time period and the uteri harvested. Number and size of the tumors are determined both the control group and the treatment group.

2. Implantation of Human Tumor Tissue in Nude Mice

Tissue from human leiomyomas are implanted into the peritoneal cavity of sexually mature, female, nude mice (immune deficient). Exogenous estrogen (estradiol, time-release pellets) is supplied to the mice to stimulate the growth of the implants. The test group receives a compound of formula I in corn oil by gastric gavage once a day. The control group receives only corn oil by gastric gavage once a day. The dosing continues for 3–16 weeks. Growth of the implants is measured by metric caliper each week.

Endometriosis Test Procedure

One hundred women suffering from diagnosed endometriosis are chosen for the study. Women in generally good health, but who are not receiving hormonal therapy (estrogens, progestins, GnRH, or danazol) for any reason are included in the study.

Since endometriosis is idiosyncratic, diagnosis is carefully made on each individual and a variety of parameters are evaluated. Analysis of each of these individual parameters from the initial entry into the study to their final exit from the study is carefully noted in order that the results of the clinical trial can be interpreted. The parameters listed may not all be essential in each case; however, there are at least several defining factors. The parameters for endometriosis which may be monitored are: pelvic pain, CT, MRI, or ultrasound scans of the pelvic area, blood levels of CA125, and/or laparoscopy. As mentioned before, each individual will have a different spectrum of symptoms which need to be followed in that individual throughout the course of the study.

Fifty women participating in the study receive 80–500 mg of a compound of the present invention per day and fifty women receive a matched placebo. The study is continued for three months. At the end of the study period, each patient is evaluated by parameters listed above and status of the endometriosis determined.

Restenosis Test Procedure

Compounds of this invention inhibit aortal smooth muscle cell proliferation, an experimental model for the inhibition of restenosis. The assay system described in U.S. Pat. No. 5,457,113 may be employed.

The following examples are provided to enable one skilled in the art to practice the invention. These examples are merely illustrative, and are not to be read as limiting the scope of the present invention as it is defined by the appended claims.

EXAMPLES

Preparation of Starting Materials

Preparation A

Preparation of 1a,2,3,4,4a,5,5,6-octahydroindeno-4aβ-methyl[3a-4,b]oxirene-2,5-dione

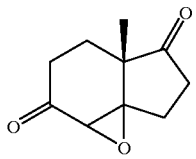

A solution of (S)-2, 3, 7, 7a-tetrahydro-7aβ-methyl-1H-indene-1,5(6H)-dione (2.00 g, 12.2 mmol), prepared as described in *Organic Synthesis,* 7: 363 (1984) in methanol (20 mL) and hydrogen peroxide (30% solution in water, 4.2 mL, 36.5 mmol).was cooled to 15° C. in a cold water bath. A solution of 5N sodium hydroxide (1.2 mL, 6.1 mmol) was added dropwise such that the reaction temperature was kept below 30° C. After the addition, the reaction was warmed to room temperature for 15 minutes. Water was added and the reaction extracted diethyl ether. The organic extracts were combined, washed with brine, dried (sodium sulfate), and concentrated to yield the title compound (1.45 g, 67%) as a colorless oil. $^1$H NMR (300 MHz, CDCl$_3$) δ1.15 (s, 3H), 1.67 (m, 1H), 1.95 (m, 1H), 2.04 (m, 1H), 2.31 (m, 1H), 2.47 (m, 1H), 2.69 (m, 3H), 3.61 (s, 1H); MS (FD) m/e 181.

Preparation B

Preparation of 1a,2,3,4,4a,5,5 6-octahydroindeno-4aα-methyl[3a-4,b]oxirene-2,5-dione

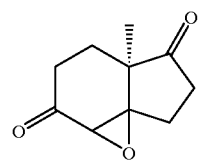

A solution of (R)-2, 3, 7, 7a-tetrahydro-7aα-methyl-1H-indene-1,5(6H)-dione (20.00 g, 121.8 mmol) (prepared as described in *Organic Synthesis,* 7: 363 (1984) in methanol (200 mL) and hydrogen peroxide (30% in water, 41.4 mL, 365.4 mmol) was cooled to 15° C. in a cold water bath. A solution of 5N sodium hydroxide (12.2 mL, 60.9 mmol) was added dropwise such that the reaction temperature was kept below 30° C. After the addition, the reaction was warmed to room temperature for 15 minutes. Water was added and the reaction extracted with diethyl ether. The organic extracts were combined, washed with brine, dried (sodium sulfate), and concentrated to yield the title compound (12.81 g, 58%) as a colorless oil. $^1$H NMR (300 MHz, CDCl$_3$) δ1.15 (s, 3H), 1.67 (m, 1H), 1.95 (m, 1H), 2.04 (m, 1H), 2.31 (m, 1H), 2.47 (m, 1H), 2.69 (m, 3H), 3.61 (s, 1H); MS (FD) m/e 181.

Preparation C

Preparation of 2,3,3a,4,5,6,7,7a-octahydro-7a-hydroxy-7-[(3-methoxyphenyl)thio]-3aβ-methyl-1H-indene-3,6-dione

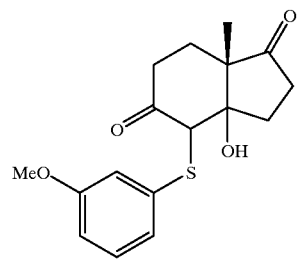

A 5N solution of sodium hydroxide (0.5 mL, 2.50 mmol) was added to a suspension of 1a,2,3,4,4a,5,5,6-octahydroindeno-4aβ-methyl[3a-4,b]oxirene-2,5-dione (1.30 g, 7.21 mmol, prepared as described above in Preparation A) and 3-methoxybenzenethiol (0.90 mL, 7.21 mmol) in water (200 mL) and the solution stirred vigorously. After 15 min., the reaction was extracted with diethyl ether. The organic extracts were combined, extracted with brine, dried over sodium sulfate, and concentrated. The resulting oil was dissolved in ethyl acetate and triturated with hexanes to yield the title compound (1.20 g, 53%) as a light orange solid. $^1$H NMR (300 MHz, CDCl$_3$) δ1.43 (s, 3H), 1.79 (m, 4H), 2.00 (bs, 1H), 2.19–2.41 (m, 4H), 2.89–3.05 (m, 2H), 3.67 (s, 1H), 3.82 (s, 3H), 6.83 (dd, J=2.0, 7.6 Hz, 1H), 7.04 (m, 2H), 7.25 (m, 1H); MS (FD) m/e 321.

Preparation D

Preparation of 2,3,3a,4,5,6,7,7a-octahydro-7a-hydroxy-7-[(3-methoxyphenyl)thiol]-3aα-methyl-1H-indene-3,6-dione

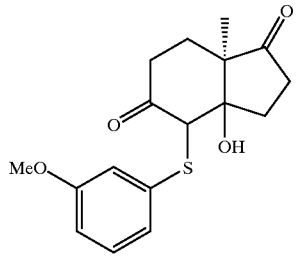

A 5N solution of sodium hydroxide (0.3 mL, 1.50 mmol) was added to a suspension of 1a,2,3,4,4a,5,5,6-octahydroindeno-4aα-methyl[3a-4,b]oxirene-2,5-dione (12.75 g, 70.75 mmol) and 3-methoxybenzenethiol (8.8 mL, 70.75 mmol, prepared as described above in Preparation B) in water (200 mL). and the solution stirred vigorously. After 15 min., the reaction was extracted with diethyl ether. The organic extracts were combined, extracted with brine, dried over sodium sulfate, and concentrated. The resulting oil was dissolved in ethyl acetate and triturated with hexanes to yield the title compound (7.79 g, 35%) as a white solid. $^1$H NMR (300 MHz, CDCl$_3$) δ1.43 (s, 3H), 1.79 (m, 4H), 2.00 (bs, 1H), 2.19–2.41 (m, 4H), 2.89–3.05 (m, 2H), 3.67 (s, 1H), 3.82 (s, 3H), 6.83 (dd, J=2.0, 7.6 Hz, 1H), 7.04 (m, 2H), 7.25 (m, 1H); MS (FD)–321.

Preparation E

Preparation of 3aβ-methyl-8-methoxy-1H-benz[b]indeno[5,4-d]thiophene-3-one

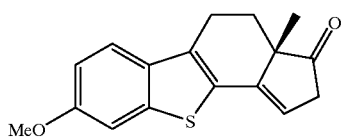

A solution of 2,3,3a,4,5,6,7,7a-octahydro-7a-hydroxy-7-[(3-methoxyphenyl)thio]-3aβ-methyl-1H-indene-3,6-dione (9.86 g, 30.73 mmol, prepared as described in Preparation C above) in anhydrous dichloromethane (500 mL) was reacted under nitrogen with aluminum chloride (16.38 g, 122.91 mmol) for 1 hour. The reaction was slowly adjusted to pH=5 with a solution of sodium bicarbonate. The reaction mixture was extracted with chloroform and the combined organic extracts were combined, washed with brine, dried over sodium sulfate, and concentrated. Crystallization from chloroform/hexane yielded the title compound (5.96 g, 68%) as red needles. $^1$H NMR (300 MHz, CDCl$_3$) δ1.26 (s, 3H), 1.70 (td, J=6.6, 12.8 Hz, 1H), 2.14 (m, 1H), 2.98 (m, 3H), 3.42 (m, 1H), 3.89 (s, 3H), 5.97 (s, 1H), 7.01 (dd, J=2.2, 8.7 Hz, 1H), 7.30 (d, J=2.3 Hz, 1H), 7.54 (d, J=8.7 Hz, 1H); MS (FD) m/e 285.

Preparation F

Preparation of 3aα-methyl-8-methoxy-1H-benz[b]indeno[5,4-d]thiophene-3-one

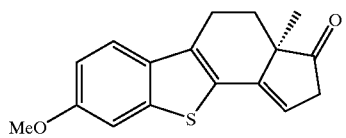

A solution of 2,3,3a,4,5,6,7,7a-octahydro-7a-hydroxy-7-[(3-methoxyphenyl)thio]-3aα-methyl-1H-indene-3,6-dione (7.77 g, 24.25 mmol, prepared as described in Preparation D above) in anhydrous dichloromethane (500 mL) was reacted under nitrogen with aluminum chloride (12.93 g, 97.01 mmol) for 1 hour. The reaction was slowly adjusted to pH=5 with a solution of sodium bicarbonate. The reaction mixture was extracted with chloroform and the combined organic extracts were combined, washed with brine, dried over sodium sulfate, and concentrated. Crystallization from chloroform/hexane yielded the title compound (3.60 g, 53%) as red needles. $^1$H NMR (300 MHz, CDCl$_3$) δ1.26 (s, 3H), 1.70 (td, J=6.6, 12.8 Hz, 1H), 2.14 (m, 1H), 2.98 (m, 3H), 3.42 (m, 1H), 3.89 (s, 3H), 5.97 (s, 1H), 7.01 (dd, J=2.2, 8.7 Hz, 1H), 7.30 (d, J=2.3 Hz, 1H), 7.54 (d, J=8.7 Hz, 1H); M (FD) m/e 285.

Embodiments of the Invention

Example 1

Preparation of 3β-Hydroxy-8-methoxy-3aβ-methyl-3,3a,4,5-tetrahydro-2H-benz[b]indeno[5,4-d]thiophene

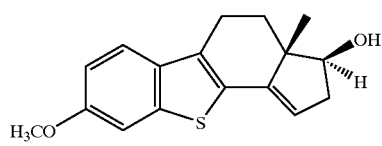

A solution of 3aβ-methyl-8-methoxy-1H-benz[b]indeno[5,4-d]thiophene-3-one (2.85 g, 10.02 mmol, prepared as described in Preparation E above) in THF (100 mL) and methanol (10 mL) was reacted with sodium borohydride (0.42 g, 11.02 mmol). After 30 min. at room temperature, the reaction was quenched with 1N HCl and extracted with ethyl acetate. The combined organic extracts were washed with brine, dried over sodium sulfate, and concentrated to yield the title compound (2.86 g, 9.99 mmol) as a light yellow solid: $^1$H NMR (300 MHz, CDCl$_3$) δ1.08 (s, 3H), 1.65 (m, 2H), 2.15 (dd, J=3.5, 10.9 Hz, 1H), 2.50 (m, 1H), 2.70–3.00 (m, 3H), 3.88 (s, 3H), 4.18 (t, J=7.9 Hz, 1H), 5.60 (s, 1H), 6.98 (dd, J=2.2, 8.8 Hz, 1H), 7.28 (d, J=2.2 Hz, 1H), 7.50 (d, J=8.8 Hz, 1H); MS (FD) m/e 286.

Example 2
Preparation of 3α-Hydroxy-8-methoxy-3aα-methyl-3,3a,4,5-tetrahydro-2H-benz[b]indeno[5,4-d]thiophene

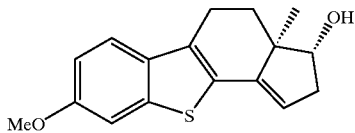

A solution of 3aα-methyl-8-methoxy-1H-benz[b]indeno[5,4-d]thiophene-3-one (3.38 g, 11.89 mmol) in THF (100 mL) and methanol (10 mL) was reacted with sodium borohydride (0.45 g, 11.89 mmol). After 30 min. at room temperature, the reaction was quenched with 1N HCl and extracted with ethyl acetate. The combined organic extracts were washed with brine, dried over sodium sulfate, and concentrated to yield the title compound (3.31 g, 97%) as a light yellow solid: $^1$H NMR (300 MHz, CDCl$_3$) δ1.08 (s, 3H), 1.65 (m, 2H), 2.15 (dd, J=3.5, 10.9 Hz, 1H), 2.50 (m, 1H), 2.70–3.00 (m, 3H), 3.88 (s, 3H), 4.18 (t, J=7.9 Hz, 1H), 5.60 (s, 1H), 6.98 (dd, J=2.2, 8.8 Hz, 1H), 7.28 (d, J=2.2 Hz, 1H), 7.50 (d, J=8.8 Hz, 1H); MS (FD)–286.

Example 3
Preparation of 3β-Hydroxy-8-methoxy-3aβ-methyl-2,3,3a,4,5,10bβ-hexahydro-1H-benz[b]indeno[5,4-d]thiophene (Example 3a) and 3β-hydroxy-8-methoxy-3aβ-methyl-2,3,3a,4,5,10bα-hexahydro-1H-benz[b]indeno[5,4-d]thiophene (Example 3b)

(Example 3a)

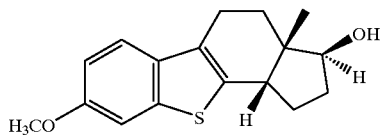

(Example 3b)

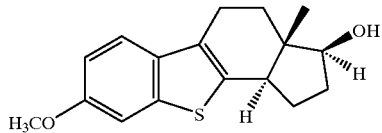

To a suspension of 5% Pd/C (1.16 g) in 1:1 ethanol/THF was dissolved 3β-hydroxy-8-methoxy-3aβ-methyl-3,3a,4,5-tetrahydro-2H-benz[b]indeno[5,4-d]thiophene (2.32 g, 8.10 mmol, prepared as described in Example 1 above) under inert atmosphere. Hydrogen was added via balloon until no starting material was present by $^1$H-NMR. To the resulting mixture was added Celite and the mixture filtered, and concentrate.

Purification by flash chromatography (silica gel, 25% ethyl acetate/hexanes) gave the title compounds (1.05 g cis (Example 3a), 0.90 g trans (Example 3b)) as clear foams:

Example 3a: $^1$H NMR (300 MHz, CDCl$_3$) δ1.12 (s, 3H), 1.60–1.80 (m, 4H), 2.19–2.38 (m, 2H), 2.72 (m, 2H), 3.04 (t, J=8.0 Hz, 1H), 3.86 (s, 3H), 3.97 (m, 1H), 6.98 (dd, J=2.6, 9.0 Hz, 1H), 7.28 (d, J=2.6 Hz, 1H), 7.47 (d, J=8.6 Hz, 1H); MS (FD)–288.

Example 3b: $^1$H NMR (300 MHz, CDCl$_3$) δ0.80 (s, 3H), 1.60–1.82 (m, 3H), 2.05 (m, 1H), 2.15 (dd, J=6.0, 7.0 Hz, 1H), 2.35 (m, 1H), 2.78–2.99 (m, 3H), 3.88 (s, 3H), 3.95 (m, 1H), 6.99 (dd, J=2.8, 9.0 Hz, 1H), 7.30 (d, J=2.3 Hz, 1H), 7.48 (d, J=8.8 Hz, 1H); MS (FD) m/e 288.

Example 4
Preparation of 3α-Hydroxy-8-methoxy-3aα-methyl-2,3,3a,4,5,10bα-hexahydro-1H-benz[b]indeno[5,4-d]thiophene (Example 4a) and 3α-hydroxy-8-methoxy-3aα-methyl-2,3,3a,4,5,10bβ-hexahydro-1H-benz[b]indeno[5,4-d]thiophene (Example 4b)

(Example 4a)

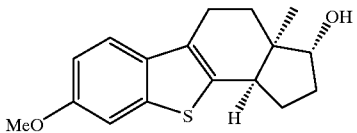

(Example 4b)

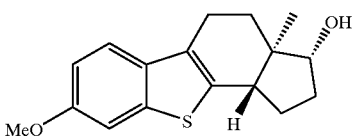

In a suspension of 5% Pd/CaCO$_3$ (1.7 g) in 1:1 methanol/THF was dissolved 3α-hydroxy-8-methoxy-3aα-methyl-3,3a,4,5-tetrahydro-2H-benz[b]indeno[5,4-d]thiophene (2.32 g, 8.10 mmol, prepared as described in Example 2 above) under inert atmosphere. Hydrogen was added via balloon until no starting material was present by $^1$H-NMR. To the resulting mixture was added Celite and the mixture filtered and concentrate. Purification by flash chromatography (silica gel, 25% ethyl acetate/hexanes) gave the title compounds (0.58 g cis (Example 4a), 2.06 g trans (Example 4b)) as clear foams:

Example 4a: $^1$H NMR (300 MHz, CDCl$_3$) δ1.12 (s, 3H), 1.60–1.80 (m, 4H), 2.19–2.38 (m, 2H), 2.72 (m, 2H), 3.04 (t, J=8.0 Hz, 1H), 3.86 (s, 3H), 3.97 (m, 1H), 6.98 (dd, J=2.6, 9.0 Hz, 1H), 7.28 (d, J=2.6 Hz, 1H), 7.47 (d, J=8.6 Hz, 1H); MS (FD)–288.

Example 4b: $^1$H NMR (300 MHz, CDCl$_3$) δ0.80 (s, 3H), 1.60–1.82 (m, 3H), 2.05 (m, 1H), 2.15 (dd, J=6.0, 7.0 Hz, 1H), 2.35 (m, 1H), 2.78–2.99 (m, 3H), 3.88 (s, 3H), 3.95 (m, 1H), 6.99 (dd, J=2.8, 9.0 Hz, 1H), 7.30 (d, J=2.3 Hz, 1H), 7.48 (d, J=8.8 Hz, 1H); MS (FD)–288.

Example 5
Preparation of 3α-Hydroxy-8-methoxy-3aβ-methyl-2,3,3a,4,5,10bα-tetrahydro-1H-benz[b]indeno[5,4-d]thiophene

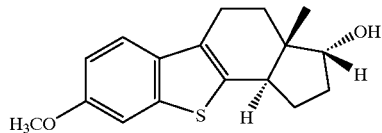

Step A. Preparation of the 4-Nitrobenzoic acid ester of 3α-hydroxy-8-methoxy-3aβ-methyl-2,3,3a,4,5,10b-hexahydro-1H-benz[b]indeno[5,4-d]thiophene To a solution of 3β-hydroxy-8-methoxy-3aβ-methyl-2,3,3a,4,5,10bβ-hexahydro-1H-benz[b]indeno[5,4-d]thiophene (0.37 g, 1.28 mmol), triphenylphosphine (0.84 g, 3.21 mmol), and p-nitrobenzoic acid (0.54 g, 3.21 mmol) in anhydrous toluene (40 mL) under nitrogen was added diethyl azodicarboxylate (0.51 mL, 3.21 mmol) dropwise. The reaction was heated to 80° C. for 45 minutes, then cooled to room temperature, concentrated, and dissolved in diethyl ether. The mixture was triturated with hexane, filtered, and the filtrate concentrated. Purification by flash chromatography (silica, 20% ethyl acetate/hexane) gave the title compound (0.39 g, 70%) as a yellow oil: ¹H NMR (300 MHz, CDCl₃) δ0.88 (s, 3H), 1.46 (m, 1H), 1.80 (m, 1H), 2.03 (m, 2H), 2.28 (m, 1H), 2.63 (m, 1H), 2.78–2.98 (m, 2H), 3.40 (m, 1H), 3.88 (s, 3H), 4.49 (m, 1H), 5.34 (d, J=6.0 Hz, 1H), 6.98 (dd, J=2.4, 8.7 Hz, 1H), 7.31, (d, J=2.3 Hz, 1H), 7.46 (d, J=8.7 Hz, 1H), 8.22 (d, j=8.9 Hz, 2H), 8.27 (d, J=8.7 Hz, 2H); MS (FD) m/e 437.

Step B. Preparation of 3α-Hydroxy-8-methoxy-3aβ-methyl-2,3,3a,4,5,10bα-tetrahydro-1H-benz[b]indeno[5,4-d]thiophene To a solution of the 4-Nitrobenzoic acid ester of 3α-hydroxy-8-methoxy-3aβ-methyl-2,3,3a,4,5,10bβ-hexahydro-1H-benz[b]indeno[5,4-d]thiophene (0.38 g, 0.87 mmol, prepared as described in Example 5, Step A above) in methanol (20 mL) and THF (5 mL) stirring at room temperature was added potassium carbonate (0.96 g, 6.95 mmol). After 1.5 h, water was added and the reaction extracted with ethyl acetate. The combine organic extracts were washed with brine, dried over sodium sulfate, and concentrate. Purification by flash chroma-tography (silica, 20% ethyl acetate/hexane) yielded the title compound (0.17 g, 69%) as a clear foam: ¹H NMR (300 MHz, CDCl) δ0.70(s, 3H), 1.55–1.91 (m, 3H), 2.05–2.22 (m, 2H), 2.45 (m, 1H), 2.83–2.97 (m, 2H), 3.26 (m, 1H), 3.88 (m, 1H), 4.02 (d, J=6.0 Hz, 1H), 6.98 (dd, J=2.6, 8.7 Hz, 1H), 7.30 (d, J=2.3 Hz, 1H), 7.46 (d, J=8.7 Hz, 1H); MS (FD) m/e 288.

Example 6
Preparation of 3β-Hydroxy-8-methoxy-3aα-methyl-2,3,3a,4,5,10bβ-tetrahydro-1H-benz[b]indeno[5,4-d]thiophene

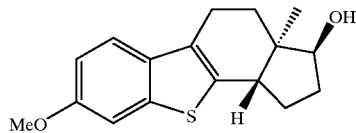

Step A. Preparation of the 4-Nitrobenzoic acid ester of 3β-hydroxy-8-methoxy-3aα-methyl-2,3,3a,4,5,10bβ-hexahydro-1H-benz[b]indeno[5,4-d]thiophene To a solution of 3a-hydroxy-8-methoxy-3aα-methyl-2,3,3a,4,5,10bβ-hexahydro-1H-benz[b]indeno[5,4-d]thiophene (1.00 g, 3.47 mmol, prepared as described in Example 4b above), triphenylphosphine (2.27 g, 8.67 ]mmol), and p-nitrobenzoic acid (1.45 g, 8.67 mmol) in anhydrous toluene (100 mL) under nitrogen was added diethyl azodicarboxylate (1.4 mL, 8.67 mmol) dropwise. The reaction was heated to 80° C. for 45 minutes, then cooled to room temperature. The reaction was concentrated and dissolved in diethyl ether. The resulting mixture was triturated with hexane, then filtered, and the filtrate concentrated. Purification by flash chromatography (silica, 20% ethyl acetate/hexane) gave the title compound (1.46 g, 96%) as a yellow oil: ¹H NMR (300 MHz, CDCl₃) δ0.88 (s, 3H), 1.46 (m, 1H), 1.80 (m, 1H), 2.03 (m, 2H), 2.28 (m, 1H), 2.63 (m, 1H), 2.78–2.98 (m, 2H), 3.40 (m, 1H), 3.88 (s, 3H), 4.49 (m, 1H), 5.34 (d, J=6.0 Hz, 1H), 6.98 (dd, J=2.4, 8.7 Hz, 1H), 7.31 (d, J=2.3 Hz, 1H), 7.46 (d, J=3.7 Hz, 1H), 8.22 (cl, j=8.9 Hz, 2H), 8.27 (d, J=8.7 Hz, 2H); MS (FD) m/e 437.

Step B. 3β-Hydroxy-8-methoxy-3aα-methyl-2,3,3a,4,5.10bβ-tetrahydro-1H-benz[b]indeno5,4-d]thiophene To a solution of 4-nitrobenzoic acid ester of 3β-hydroxy-8-methoxy-3aα-methyl-2,3,3a,4,5,10bβ-hexahydro-1H-5 benz[b]indeno[5,4-d]thiophene (1.46 g, 3.34 mmol, prepared as described in Step A above) stirring in methanol (60 mL) and THF (15 mL) at room temperature was added potassium carbonate (3.94 g, 28.52 mmol). After 2 h, water was added and the reaction extracted with ethyl acetate. The combined organic extracts were washed with brine, dried over sodium sulfate, and concentrate. Purification by flash chromatography (silica, 20% ethyl acetate/hexane) yielded the title compound (0.56 g, 54%) as a clear foam: ¹H NMR (300 MHz, CDCl₃) δ0.70 (s, 3H), 1.55–1.91 (m, 3H), 2.05–2.22 (m, 2H), 2.45 (m, 1H), 2.83–2.97 (m, 2H), 3.26 (m, 1H), 3.88 (m, 1H), 4.02 (d, J=6.0 Hz, 1H), 6.98 (dd, J=2.6, 8.7 Hz, 1H), 7.30 (d, J=2.3 Hz, 1H), 7.46 (d, J=8.7 Hz, 1H); MS (FD) m/e 288.

Example 7
Preparation of 3β,8-Dihydroxy-3aβ-methyl-2,3,3a,4,5,10bβ-tetrahydro-1H-benz[b]indeno[5,4-d]thiophene

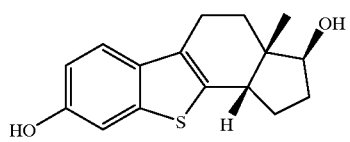

To a solution of 3β-hydroxy-8-methoxy-3aβ-methyl-2,3,3a,4,5,10bβ-hexahydro-1H-benz[b]indeno[5,4-d]thiophene (0.60 g, 2.08 mmol, prepared as described in Example 3a above) stirring in DMF (100 mL) at room temperature was added sodium ethane thiol (0.97 g, 10.40 mmol) and the mixture heated to reflux. After 2 h, the mixture was cooled to room temperature, concentrated and extracted with ethyl acetate. The combined organic extracts were combined, washed with brine, dried over sodium sulfate, and concentrate. Purification by flash chromatography (silica, 40% ethyl acetate/hexanes) gave the title compound (0.55 g, 97%) as a clear foam: ¹H NMR (300 MHz, CDCl₃) δ1.12(s, 1H), 1.60–1.85 (m, 4H), 2.18–2.42 (m, 2H), 2.73 (m, 2H), 3.01 (t, J=8.0 Hz, 1H), 3.99 (t, J=4.1 Hz, 1H), 5.20 (bs, 1H), 6.90 (dd, J=2.3, 8.6 Hz, 1H), 7.22 (d, J=2.3 Hz, 1H), 7.43 (d, J=8.6 Hz, 1H); MS (FD) m/e 274.

Example 8
Preparation of 3β,8-Dihydroxy-3aβ-methyl-2,3,3a,4,5,10bα-tetrahydro-1H-benz[b]indeno[5,4-d]thiophene

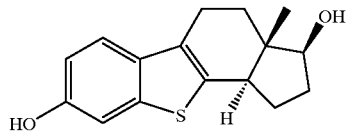

A solution of 3β-hydroxy-8-methoxy-3aβ-methyl-2,3,3a,4,5,10bα-hexahydro-1H-benz[b]indeno[5,4-d]thiophene (0.60 g; 2.08 mmol, prepared as described in Example 3b above) and sodium ethane thiol (0.97 g, 10.40 mmol) in anhydrous DMF (60 mL) was heated under reflux for 45 minutes. The reaction was concentrated and extracted with ethyl acetate. The combined organic extracts were washed with brine, dried over sodium sulfate, and concentrate. Purification by chromatography (silica, 30% ethyl acetate/hexanes) gave the title compound (0.17 g, 30%) as a clear foam: ¹H NMR (300 MHz, CDCl₃) δ0.73 (s, 3H), 1.64– 1.80 (m, 4H), 2.15 (m, 2H), 2.85 (m, 2H), 2.94 (s, 1H), 3.98 (m, 2H), 6.91 (dd, J=2.2, 8.4 Hz, 1H), 7.25 (d, J=2.2 Hz, 1H), 7.40 (d, J=8.6 Hz, 1H), 8.35 (s, 1H); MS (FD) m/e 274.

Example 9
Preparation of 3α,8-Dihydroxy-3aβ-methyl-2,3,3a,4,5,10bα-tetrahydro-1H-benz[b]indeno[5,4-d]thiophene

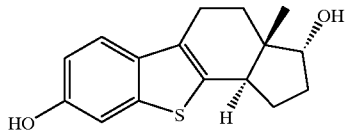

A solution of 3α-Hydroxy-8-methoxy-3aβ-methyl-2,3,3a,4,5,10bα-tetrahydro-1H-benz[b]indeno[5,4-d]thiophene (0.45 g, 1.56 mmol, prepared as described in Example 5 above) and sodium ethane thiol (0.65 g, 7.80 mmol) in anhydrous DMF (50 mL) was heated under reflux for 60 minutes. The reaction was cooled to room temperature, concentrated, and extracted with ethyl acetate. The combined organic extracts were combined, extracted with brine, dried over sodium sulfate, and concentrate. Purification by chromatography (silica, 30% ethyl acetate/hexanes) gave the title compound (0.25 g, 58%) as a clear foam: $^1$H NMR (300 MHz, CDCl$_3$) δ0.63 (s, 3H), 1.51–1.94 (m, 3H), 2.10–2.29 (m, 2H), 2.43 (m, 1H), 2.72–2.87 (m, 2H), 3.05 (bs, 2H), 3.23 (m, 2H), 4.01 (m, 1H), 6.92 (dd, J=2.2, 8.9 Hz, 1H), ,7.25 (d, J=2.2 Hz, 1H), 7.41 (d, J=8.5 Hz, 1H), 8.43 (s, 1H); MS (FD) m/e 274.

Example 10
Preparation of 3α,8-Dihydroxy-3aα-methyl-2,3,3a,4,5,10bα-tetrahydro-1H-benz[b]indeno[5,4-d]thiophene

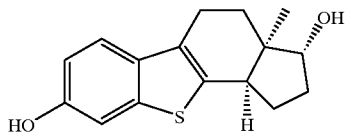

A solution of 3α-hydroxy-8-methoxy-3aα-methyl-2,3,3a,4,5,10bα-hexahydro-1H-benz[b]indeno[5,4-d]thiophene (0.48 g, 1.66 mmol, prepared as described in Example 4a above) and sodium ethane thiol (0.79 g, 8.33 mmol) in anhydrous DMF (50 mL) was heated under ref lux for 60 minutes. The reaction was concentrated and extracted with ethyl acetate. The combined organic extracts were combined, extracted with brine, dried over sodium sulfate, and concentrate. Purification by chromatography (silica, 40% ethyl acetate/hexanes) gave the title compound (0.25 g, 55%) as a clear foam: $^1$H NMR (300 MHz, CDCl$_3$) δ1.12(s, 1H), 1.60–1.85 (m, 4H), 2.18–2.42 (m, 2H), 2.73 (m, 2H), 3.01 (t, J=8.0 Hz, 1H), 3.99 (t, J=4.1 Hz, 1H), 5.20 (bs, 1H), 6.90 (dd, J=2.3, 8.6 Hz, 1H), 7.22 (d, J=2.3 Hz, 1H), 7.43 (d, J=8.6 Hz, 1H); MS (FD) m/e 274.

Example 11
Preparation of 3α,8-Dihydroxy-3aα-methyl-2,3,3a,4,5,10bβ-tetrahydro-1H-benz[b]indeno[5,4-d]thiophene

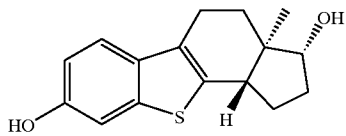

A solution of 3aα-hydroxy-8-methoxy-3aα-methyl-2,3,3a,4,5,10bβ-hexahydro-1H-benz[b]indeno[5,4-d]thiophene (0.50 g, 1.73 mmol, prepared as described in Example 4b above) and sodium ethane thiol (0 .81 g, 8.65 mmol) in anhydrous DMF (50 mL) was heated under reflux for 30 minutes. The reaction was then concentrated and extracted with ethyl acetate. The combined organic extracts were combined, washed with brine, dried over sodium sulfate, and concentrate. Purification by radial chromatography (silica, 40% ethyl acetate/hexanes) gave the title compound (0.10 g, 21%) as a clear foam: $^1$H NMR (300 MHz, CDCl$_3$) δ0.73 (s, 3H), 1.64–1.80 (m, 4H), 2.15 (m, 2H), 2.85 (m, 2H), 2.94 (s, 1H), 3.98 (m, 2H), 6.91 (dd, J=2.2, 8.4 Hz, 1H), 7.25 (d, J=2.2 Hz, 1H), 7.40 (d, J=8.6 Hz, 1H), 8.35 (s, 1H); MS (FD) m/e 274.

We claim:

1. A compound selected from the group consisting of the individual stereoisomers of a compound of the formula

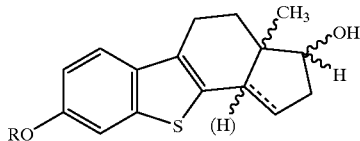

wherein

R is hydrogen or straight or branched alkyl of one to four carbon atoms;

the dotted line represents an optional double bond; and the parenthetic hydrogen atom is absent when the optional double bond is present.

2. An individual stereoisomer of a compound as defined by claim 1 having the structure

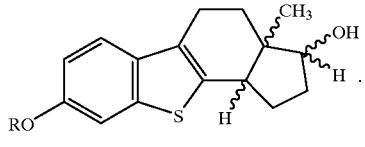

3. An individual stereoisomer of a compound as defined by claim 1 having the structure

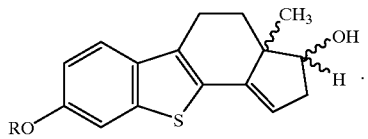

4. A compound as defined by claim 1 wherein R is hydrogen.

5. A compound as defined by claim 1 wherein R is alkyl of one to four carbon atoms.

6. A compound as defined by claim 2 selected from the group consisting of

3α-hydroxy-8-methoxy-3aα-methyl-2,3,3a,4,5,10bα-hexahydro-1H-benz[b]indeno[5,4-d]thiophene;

3α-hydroxy-8-methoxy-3aα-methyl-2,3,3a,4,5,10bβ-hexahydro-1H-benz[b]indeno[5,4-d]thiophene;

3α-hydroxy-8-methoxy-3aβ-methyl-2,3,3a,4,5,10bα-hexahydro-1H-benz[b]indeno[5,4-d]thiophene;

3α-hydroxy-8-methoxy-3aβ-methyl-2,3,3a,4,5,10bβ-hexahydro-1H-benz[b]indeno[5,4-d]thiophene;

3β-hydroxy-8-methoxy-3aα-methyl-2,3,3a,4,5,10bα-hexahydro-1H-benz[b]indeno[5,4-d]thiophene;

3β-hydroxy-8-methoxy-3aα-methyl-2,3,3a,4,5,10bβ-hexahydro-1H-benz[b]indeno[5,4-d]thiophene;

3β-hydroxy-8-methoxy-3aβ-methyl-2,3,3a,4,5,10bα-hexahydro-1H-benz[b]indeno[5,4-d]thiophene;

3β-hydroxy-8-methoxy-3aβ-methyl-2,3,3a,4,5,10bβ-hexahydro-1H-benz[b]indeno[5,4-d]thiophene;

3α,8-dihydroxy-3aα-methyl-2,3,3a,4,5,10bα-hexahydro-benz[b]indeno[5,4-d]thiophene;

3α,8-dihydroxy-3aα-methyl-2,3,3a,4,5,10bβ-hexahydro-1H-benz[b]indeno[5,4-d]thiophene;

3α,8-dihydroxy-3aβ-methyl-2,3,3a,4,5,10bα-hexahydro-1H-benz[b]indeno[5,4-d]thiophene;

3α,8-Dihydroxy-3aβ-methyl-2,3,3a,4,5,10bβ-hexahydro-1H-benz[b]indeno[5,4-d]thiophene;

3β,8-dihydroxy-3aα-methyl-2,3,3a,4,5,10bα-hexahydro-1H-benz[b]indeno[5,4-d]thiophene;

3β,8-dihydroxy-3aα-methyl-2,3,3a,4,5,10bβ-hexahydro-1H-benz[b]indeno[5,4-d]thiophene;

3β,8-Dihydroxy-3aβ-methyl-2,3,3a,4,5,10bα-hexahydro-1H-benz[b]indeno[5,4-d]thiophene; and 3β,8-dihydroxy-3aβ-methyl-2,3,3a,4,5,10bβ-hexahydro-1H-benz[b]indeno[5,4-d]thiophene.

7. A compound as defined by claim 3 selected from the group consisting of

3α-Hydroxy-8-methoxy-3aα-methyl-3,3a,4,5-tetrahydro-2H-benz[b]indeno[5,4-d]thiophene;

3α-Hydroxy-8-methoxy-3aβ-methyl-3,3a,4,5-tetrahydro-2H-benz[b]indeno[5,4-d]thiophene;

3β-Hydroxy-8-methoxy-3aα-methyl-3,3a,4,5-tetrahydro-2H-benz[b]indeno[5,4-d]thiophene;

3β-Hydroxy-8-methoxy-3aβ-methyl-3,3a,4,5-tetrahydro-2H-benz[b]indeno[5,4-d]thiophene;

3α,8-Dihydroxy-3aα-methyl-3,3a,4,5-tetrahydro-2H-benz[b]indeno[5,4-d]thiophene;

3α,8-Diydroxy-3aβ-methyl-3,3a,4,5-tetrahydro-2H-benz[b]indeno[5,4-d]thiophene;

3β,8-Dihydroxy-3aα-methyl-3,3a,4,5-tetrahydro-2H-benz[b]indeno[5,4-d]thiophene; and 3β,8-Dihydroxy-3aα-methyl-3,3a,4,5-tetrahydro-2H-benz[b]indeno[5,4-d]thiophene.

8. A pharmaceutical formulation for the treatment of estrogen-related disorders in a female comprising a therapeutically effective amount of a compound as defined in claim 1 in combination with a pharmaceutically acceptable carrier.

9. A method of treating estrogen-related disorders selected from the group consisting of estrogen-dependent cancer, uterine fibrosis, and endometriosis in a female comprising administering to a female in need of such treatment an effective amount of a compound as defined in claim 1.

10. A method as defined in claim 9 wherein said method is the treatment of estrogen-dependent breast cancer.

11. A method as defined in claim 9 wherein said method is the treatment of uterine fibrosis.

12. A method as defined in claim 9 wherein said method is the treatment of endometriosis.

\* \* \* \* \*